(12) United States Patent
Fesik et al.

(10) Patent No.: US 7,226,992 B1
(45) Date of Patent: Jun. 5, 2007

(54) MUTANT BCL-2 PROTEINS AND USES THEREOF

(75) Inventors: Stephen W. Fesik, Gurnee, IL (US); Andrew M. Petros, Mundelein, IL (US); Ho Sup Yoon, Vernon Hills, IL (US); David G. Nettesheim, Lake Forest, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/716,395

(22) Filed: Nov. 20, 2000

(51) Int. Cl.
| | |
|---|---|
| *C07K 1/00* | (2006.01) |
| *C07K 2/00* | (2006.01) |
| *C07K 4/00* | (2006.01) |
| *C07K 16/00* | (2006.01) |
| *C07K 17/00* | (2006.01) |
| *C07K 14/00* | (2006.01) |
| *A61K 8/00* | (2006.01) |
| *C12Q 1/00* | (2006.01) |
| *G01N 1/00* | (2006.01) |
| *G01N 21/00* | (2006.01) |
| *G01N 21/75* | (2006.01) |
| *G01N 21/76* | (2006.01) |
| *G01N 33/00* | (2006.01) |
| *G01N 33/53* | (2006.01) |

(52) U.S. Cl. ............... 530/350; 530/300; 530/326
(58) Field of Classification Search ........... 530/300, 530/326, 350
See application file for complete search history.

(56) References Cited

U.S. PATENT DOCUMENTS 5,646,008 A * 7/1997 Thompson et al.
6,214,986 B1 * 4/2001 Bennett et al.

OTHER PUBLICATIONS

Lazar. Transforming growth factor alpha: mutation aspartic acid 47 and leucine 48 results in different biological activities Molecular and Cellular Biology 8(3): 1247-1252, Mar. 1988.*
Gencore database sheets (four sheets) for Muchmore et al. (1996) and Boise et al. (1993), references C3 and C7 provided with IDS, respectively.*
Gencore databases sheets (two sheets) for U.S. patents 6,214,986 (Apr. 10, 2001) and 5,646,008 (Jul. 8, 1997).*

Tsujimoto, Y. et al., "Analysis of the Structure, Transcripts, and Protein Products of BCL-2, the Gene Involved in Human Follicular Lymphoma," Proceedings of the National Academy of Sciences of USA, vol. 83, (Jul. 1, 1986), pp. 5214-5218, XP000673572.
Anderson, M. et al., "Refolding, Purification, and Characterization of a Loop Deletion Mutant of Human BCL-2 From Bacterial Inclusion Bodies," Protein Expression and Purification, vol. 15, No. 2, (Mar. 1999), pp. 162-170 XP000927994.
Muchmore, S.W., et al., "X-ray and NMR Structure of Human Bcl-xL, and Inhibitor of Programmed Cell Death," Nature, vol. 381, (May 23, 1996), pp. 335-341, XP002111426.
Ottilie, S., et al., "Dimerization Properties of Human BAD," Journal of Biological Chemistry, vol. 272, No. 49, (Dec. 5, 1997), pp. 30866-30872 , XP002198263.
Anderson, et al., *Protein Expression and Purification, Refolding, Purification and Characterization of Deletion Mutant of Human Bcl-2 From Bacterial Bodies*; 15:162-170 (1999).
Bakshi, et al., *Cell, Cloning the Chromosomal Breakpoint of t(14;18) Human Lymphomas: Clustering Around $J_h$ on Chromosome 14 and Near a Transcriptional Unit on 18*; 41:899-906 (1985).
Boise, et al., *Cell, bcl-x, a bcl-2-Related Gene that Functions as a Dominant Regulator of Apoptotic Cell Death*, 74:597-608 (1993).
Cleary, M., et al., *PNAS, Nucleotide Sequence of a t(14;18) Chromosomal Breakpoint in Follicular Lymphoma and Demonstration of a Breakpoint-Cluster Region Near Transcriptionally Active Locus on Chromosome 18*, 82:7439-7443 (1985).
Cleary, M., et al., *Cell, Cloning and Structural Analysis of cDNAs for bcl-2 and a Hybrid bcl-02/Immunoglobin Transcript Resulting from the t(14;18) Translocation*, 47:19-28 (1986).
Kelekar, et al., *Molecular and Cellular Biology, Bad is a BH3 Domain-Containing Protein that Forms an Inactivating Dimer with $Bcl-x_L$* 17(12):7040-7046 (1997).
Muchmore, et al., *Nature, X-Ray and NMR Structure of Human $Bcl-x_L$ an Inhibitor of Programmed Cell Death*, 381:335-341 (1996).
Ottilie, S., et al., *J. of Biol. Chem., Dimerization Properties of Human BAD*, 272(49):30866-30872 (1997).
Sattler, M., et al., *Science, Structure of $Bcl-x_L$ _Bak Peptide Complex: Recognition Between Regulators of Apoptosis*; 275:983-986 (1997).
Seto, et al., *EMBO J., Alternative Promoters and Exons, Somatic Mutation and Deregulation of the Bcl-2-lg Fusion Gene in Lymphoma*, 7:123-131 (1988).
Tsujimoto, et al., *PNAS, Analysis of the Structure, Transcripts, and Protein Products of bcl-2, the Gene Involved in Human Follicular Lymphoma*, 83:5214-5218 (1986).
Yang, et al., *Cell, Bad, a Heterodimeric Partner for $Bcl-x_L$ and Bcl-2, Displaces Bax and Promotes Cell Death*, 80:285-291 (1995).

* cited by examiner

*Primary Examiner*—Alana M. Harris (57) ABSTRACT

Mutant peptides derived from wild-type human Bcl-2 are disclosed. Assays to identify substances which block the ability of Bcl-2 to inhibit apoptosis also are disclosed.

1 Claim, 3 Drawing Sheets

|            | 1                                                              | 50 |
|------------|----------------------------------------------------------------|----|
| Bcl-2/iso1 | MAHAGRTGYD NREIVMKYIH YKLSQRGYEW DAGDVGAAPP GAAPAPGIFS          |    |
| Bcl-2/iso2 | MAHAGRTGYD NREIVMKYIH YKLSQRGYEW DAGDVGAAPP GAAPAPGIFS          |    |
| Bcl-2/iso3 | MAHAGRTGYD NREIVMKYIH YKLSQRGYEW DAGDVGAAPP GAAPAPGFFS          |    |
| Bcl-xL    | MSMAMSQS NRELVVDFLS YKLSQKGYEW SQFS<u>DVEENR TEAPEETESE</u>     |    |

|            | 51                                                                  | 100 |
|------------|---------------------------------------------------------------------|-----|
| Bcl-2/iso1 | SQPGHTPHPA ASRDPVARTS PLQTPAAPGA AAGPALSPVP PVVHLALRQA               |     |
| Bcl-2/iso2 | SQPGHTPHPA ASRDPVARTS PLQTPAAPGA AAGPALSPVP PVVHLTLRQA               |     |
| Bcl-2/iso3 | SQPGHTPHPA ASRDPVARTS PLQTPAAPGA AAGPALSPVP PVVHLTLRQA               |     |
| Bcl-xL    | <u>METPSAINGN PSWHLADSPA VNGATGHSSS LDAREVIP-M</u> AAVKQALREA        |     |

|            | 101                                                            | 150 |
|------------|----------------------------------------------------------------|-----|
| Bcl-2/iso1 | GDDFSRRYRG DFAEMSSQLH LTPFTARGRF ATVVEELFRD GVNWGRIVAF          |     |
| Bcl-2/iso2 | GDDFSRRYRR DFAEMSSQLH LTPFTARGRF ATVVEELFRD GVNWGRIVAF          |     |
| Bcl-2/iso3 | GDDFSRRYRR DFAEMSSQLH LTPFTARGRF ATVVEELFRD GVNWGRIVAF          |     |
| Bcl-xL    | GDEFELRYRR AFSDLTSQLH ITPGTAYQSF EQVVNELFRD GVNWGRIVAF          |     |

|            | 151                                                            | 200 |
|------------|----------------------------------------------------------------|-----|
| Bcl-2/iso1 | FEFGGVMCVE SVNREMSPLV DNIALWMTEY LNRHLHTWIQ DNGGWDAFVE          |     |
| Bcl-2/iso2 | FEFGGVMCVE SVNREMSPLV DNIALWMTEY LNRHLHTWIQ DNGGWDAFVE          |     |
| Bcl-2/iso3 | FEFGGVMCVE SVNREMSPLV DNIALWMTEY LNRHLHTWIQ DNGGWDAFVE          |     |
| Bcl-xL    | FSFGGALCVE SVDKEMQVLV SRIAAWMATY LNDHLEPWIQ ENGGWDTFVE          |     |

|            | 201                                               | 239 |
|------------|---------------------------------------------------|-----|
| Bcl-2/iso1 | LYGPSMRPLF DFSWLSLKTL LSLALVGACI TLGAYLGHK         |     |
| Bcl-2/iso2 | LYGPSMRPLF DFSWLSLKTL LSLALVGACI TLGAYLGHK         |     |
| Bcl-2/iso3 | LYGPSMRPLF DFSWLSLKTL LSLALVGACI TLGAYLGHK         |     |
| Bcl-xL    | LYGNNAAAES RKGQERFNRW FLTGMTVAGV VLLGSLFSRK        |     |

SEQUENCE LISTING

```
<160> NUMBER OF SEQ ID NOS: 37

<210> SEQ ID NO 1
<211> LENGTH: 16
<212> TYPE: PRT
<213> ORGANISM: Homo sapiens

<400> SEQUENCE: 1

Asp Val Glu Glu Asn Arg Thr Glu Ala Pro Glu Gly Thr Glu Ser Glu
1               5                   10                  15

<210> SEQ ID NO 2
<211> LENGTH: 166
<212> TYPE: PRT
<213> ORGANISM: Homo sapiens

<400> SEQUENCE: 2

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Asp Val Glu Glu Asn Arg Thr Glu Ala Pro Glu Gly Thr Glu
        35                  40                  45

Ser Glu Val Val His Leu Ala Leu Arg Gln Ala Gly Asp Asp Phe Ser
    50                  55                  60

Arg Arg Tyr Arg Gly Asp Phe Ala Glu Met Ser Ser Gln Leu His Leu
65                  70                  75                  80

Thr Pro Phe Thr Ala Arg Gly Arg Phe Ala Thr Val Val Glu Glu Leu
                85                  90                  95

Phe Arg Asp Gly Val Asn Trp Gly Arg Ile Val Ala Phe Phe Glu Phe
            100                 105                 110

Gly Gly Val Met Cys Val Glu Ser Val Asn Arg Glu Met Ser Pro Leu
        115                 120                 125

Val Asp Asn Ile Ala Leu Trp Met Thr Glu Tyr Leu Asn Arg His Leu
    130                 135                 140

His Thr Trp Ile Gln Asp Asn Gly Gly Trp Asp Ala Phe Val Glu Leu
145                 150                 155                 160
```

Tyr Gly Pro Ser Met Arg
                165

<210> SEQ ID NO 3
<211> LENGTH: 239
<212> TYPE: PRT
<213> ORGANISM: Homo sapiens

<400> SEQUENCE: 3

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 4
<211> LENGTH: 239
<212> TYPE: PRT
<213> ORGANISM: Homo sapiens

<400> SEQUENCE: 4

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

```
Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
210                 215                 220

Leu Val Gly Ala Cys Ile Thr Leu Gly Ala Tyr Leu Gly His Lys
225                 230                 235

<210> SEQ ID NO 5
<211> LENGTH: 239
<212> TYPE: PRT
<213> ORGANISM: Homo sapiens

<400> SEQUENCE: 5

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Phe
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
210                 215                 220
```

```
Leu Val Gly Ala Cys Ile Thr Leu Gly Ala Tyr Leu Gly His Lys
225                 230                 235
```

<210> SEQ ID NO 6
<211> LENGTH: 237
<212> TYPE: PRT
<213> ORGANISM: Homo sapiens

<400> SEQUENCE: 6

```
Met Ser Met Ala Met Ser Gln Ser Asn Arg Glu Leu Val Val Asp Phe
1               5                   10                  15

Leu Ser Tyr Lys Leu Ser Gln Lys Gly Tyr Ser Trp Ser Gln Phe Ser
                20                  25                  30

Asp Val Glu Glu Asn Arg Thr Glu Ala Pro Glu Gly Thr Glu Ser Glu
            35                  40                  45

Met Glu Thr Pro Ser Ala Ile Asn Gly Asn Pro Ser Trp His Leu Ala
50                  55                  60

Asp Ser Pro Ala Val Asn Gly Ala Thr Gly His Ser Ser Ser Leu Asp
65                  70                  75                  80

Ala Arg Glu Val Ile Pro Met Ala Ala Val Lys Gln Ala Leu Arg Glu
                85                  90                  95

Ala Gly Asp Glu Phe Glu Leu Arg Tyr Arg Arg Ala Phe Ser Asp Leu
            100                 105                 110

Thr Ser Gln Leu His Ile Thr Pro Gly Thr Ala Tyr Gln Ser Phe Glu
        115                 120                 125

Gln Val Val Asn Glu Leu Phe Arg Asp Gly Val Asn Trp Gly Arg Ile
    130                 135                 140

Val Ala Phe Phe Ser Phe Gly Gly Ala Leu Cys Val Glu Ser Val Asp
145                 150                 155                 160

Lys Glu Met Gln Val Leu Val Ser Arg Ile Ala Ala Trp Met Ala Thr
                165                 170                 175

Tyr Leu Asn Asp His Leu Glu Pro Trp Ile Gln Glu Asn Gly Gly Trp
            180                 185                 190

Asp Thr Phe Val Glu Leu Tyr Gly Asn Asn Ala Ala Ala Glu Ser Arg
        195                 200                 205

Lys Gly Gln Glu Arg Phe Asn Arg Trp Phe Leu Thr Gly Met Thr Val
    210                 215                 220

Ala Gly Val Val Leu Leu Gly Ser Leu Phe Ser Arg Lys
225                 230                 235
```

<210> SEQ ID NO 7
<211> LENGTH: 43
<212> TYPE: DNA
<213> ORGANISM: Artificial Sequence
<220> FEATURE:
<223> OTHER INFORMATION: primer

<400> SEQUENCE: 7
cactcaccat atggctcacg ctgggagaac ggggtacgac aac        43

<210> SEQ ID NO 8
<211> LENGTH: 43
<212> TYPE: DNA
<213> ORGANISM: Artificial Sequence
<220> FEATURE:
<223> OTHER INFORMATION: primer

<400> SEQUENCE: 8

-continued gcgagctctc gagcttcaga gacagccagg agaaatcaaa cag            43

<210> SEQ ID NO 9
<211> LENGTH: 48
<212> TYPE: DNA
<213> ORGANISM: Artificial Sequence
<220> FEATURE:
<223> OTHER INFORMATION: primer

<400> SEQUENCE: 9
gccccagaag ggactgaatc ggaggtggtc cacctggccc tccgccaa       48

<210> SEQ ID NO 10
<211> LENGTH: 48
<212> TYPE: DNA
<213> ORGANISM: Artificial Sequence
<220> FEATURE:
<223> OTHER INFORMATION: primer

<400> SEQUENCE: 10
ctcagtacgg ttctcttcca catcatctcc cgcatcccac tcgtagcc       48

<210> SEQ ID NO 11
<211> LENGTH: 43
<212> TYPE: DNA
<213> ORGANISM: Artificial Sequence
<220> FEATURE:
<223> OTHER INFORMATION: primer

<400> SEQUENCE: 11
cactcaccat atggctcacg ctgggagaac ggggtacgac aac            43

<210> SEQ ID NO 12
<211> LENGTH: 50
<212> TYPE: DNA
<213> ORGANISM: Artificial Sequence
<220> FEATURE:
<223> OTHER INFORMATION: primer

<400> SEQUENCE: 12
gcgaagctct cgagctatca atcaaacaga ggccgcatgc tggggccgta     50

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
gaggtggtcc acctgaccct ccgccaagcc g                         31

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
cggcttggcg gagggtcagg tggaccacct c                         31

<210> SEQ ID NO 15
<211> LENGTH: 26
<212> TYPE: DNA
<213> ORGANISM: Artificial Sequence

```
<220> FEATURE:
<223> OTHER INFORMATION: primer

<400> SEQUENCE: 15
gccgctaccg ccgcgacttc gccgag                                          26

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
ctcggcgaag tcgcggcggt agcggc                                          26

<210> SEQ ID NO 17
<211> LENGTH: 25
<212> TYPE: PRT
<213> ORGANISM: Artificial Sequence
<220> FEATURE:
<223> OTHER INFORMATION: peptide

<400> SEQUENCE: 17

Ala Ala Ala Ala Ala Gln Arg Tyr Gly Arg Glu Leu Arg Arg Met Ser
 1               5                  10                  15

Asp Glu Phe Val Asp Ser Phe Lys Lys
            20                  25

<210> SEQ ID NO 18
<211> LENGTH: 24
<212> TYPE: PRT
<213> ORGANISM: Artificial Sequence
<220> FEATURE:
<223> OTHER INFORMATION: peptide

<400> SEQUENCE: 18

Ala Ala Ala Ala Ala Gln Arg Tyr Gly Arg Glu Leu Arg Arg Met Ser
 1               5                  10                  15

Asp Glu Phe Val Asp Ser Lys Lys
            20

<210> SEQ ID NO 19
<211> LENGTH: 18
<212> TYPE: PRT
<213> ORGANISM: Artificial Sequence
<220> FEATURE:
<223> OTHER INFORMATION: peptide

<400> SEQUENCE: 19

Ala Ala Gln Arg Tyr Gly Arg Glu Leu Arg Arg Met Ser Asp Glu Phe
 1               5                  10                  15

Val Arg

<210> SEQ ID NO 20
<211> LENGTH: 25
<212> TYPE: PRT
<213> ORGANISM: Artificial Sequence
<220> FEATURE:
<223> OTHER INFORMATION: peptide

<400> SEQUENCE: 20

Asn Leu Trp Ala Ala Gln Arg Tyr Gly Arg Glu Leu Arg Arg Met Ser
 1               5                  10                  15
```

Asp Glu Phe Val Asp Ser Phe Lys Lys
            20                  25

<210> SEQ ID NO 21
<211> LENGTH: 25
<212> TYPE: PRT
<213> ORGANISM: Artificial Sequence
<220> FEATURE:
<223> OTHER INFORMATION: peptide

<400> SEQUENCE: 21

Ala Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 22
<211> LENGTH: 25
<212> TYPE: PRT
<213> ORGANISM: Artificial Sequence
<220> FEATURE:
<223> OTHER INFORMATION: peptide

<400> SEQUENCE: 22

Asn Ala Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 23
<211> LENGTH: 25
<212> TYPE: PRT
<213> ORGANISM: Artificial Sequence
<220> FEATURE:
<223> OTHER INFORMATION: peptide

<400> SEQUENCE: 23

Asn Leu Ala Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 24
<211> LENGTH: 25
<212> TYPE: PRT
<213> ORGANISM: Artificial Sequence
<220> FEATURE:
<223> OTHER INFORMATION: peptide

<400> SEQUENCE: 24

Asn Leu Trp Gly Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 25
<211> LENGTH: 25
<212> TYPE: PRT
<213> ORGANISM: Artificial Sequence
<220> FEATURE:
<223> OTHER INFORMATION: peptide

<400> SEQUENCE: 25

Asn Leu Trp Ala Gly Gln Arg Tyr Gly Arg Glu Leu Arg Arg Met Ser
1               5                   10                  15

-continued

Asp Glu Phe Val Asp Ser Phe Lys Lys
            20                  25

<210> SEQ ID NO 26
<211> LENGTH: 25
<212> TYPE: PRT
<213> ORGANISM: Artificial Sequence
<220> FEATURE:
<223> OTHER INFORMATION: peptide

<400> SEQUENCE: 26

Asn Leu Trp Ala Ala Gln Arg Tyr Gly Arg Glu Leu Arg Arg Met Ser
 1               5                  10                  15

Asp Glu Phe Val Asp Ala Phe Lys Lys
            20                  25

<210> SEQ ID NO 27
<211> LENGTH: 25
<212> TYPE: PRT
<213> ORGANISM: Artificial Sequence
<220> FEATURE:
<223> OTHER INFORMATION: peptide

<400> SEQUENCE: 27

Asn Leu Trp Ala Ala Gln Arg Tyr Gly Arg Glu Leu Arg Arg Met Ser
 1               5                  10                  15

Asp Glu Phe Val Asp Ser Ala Lys Lys
            20                  25

<210> SEQ ID NO 28
<211> LENGTH: 25
<212> TYPE: PRT
<213> ORGANISM: Artificial Sequence
<220> FEATURE:
<223> OTHER INFORMATION: peptide

<400> SEQUENCE: 28

Asn Leu Trp Ala Ala Gln Arg Tyr Gly Arg Glu Leu Arg Arg Met Ser
 1               5                  10                  15

Asp Glu Phe Val Asp Ser Phe Ala Lys
            20                  25

<210> SEQ ID NO 29
<211> LENGTH: 25
<212> TYPE: PRT
<213> ORGANISM: Artificial Sequence
<220> FEATURE:
<223> OTHER INFORMATION: peptide

<400> SEQUENCE: 29

Asn Leu Trp Ala Ala Gln Arg Tyr Gly Arg Glu Leu Arg Arg Met Ser
 1               5                  10                  15

Asp Glu Phe Val Asp Ser Phe Lys Ala
            20                  25

<210> SEQ ID NO 30
<211> LENGTH: 25
<212> TYPE: PRT
<213> ORGANISM: Artificial Sequence
<220> FEATURE:
<223> OTHER INFORMATION: peptide

<400> SEQUENCE: 30

Gly Gly Gly Ala Ala Gln Arg Tyr Gly Arg Glu Leu Arg Arg Met Ser

```
                1               5                  10                 15
Asp Glu Phe Val Asp Ser Phe Lys Lys
            20              25

<210> SEQ ID NO 31
<211> LENGTH: 25
<212> TYPE: PRT
<213> ORGANISM: Artificial Sequence
<220> FEATURE:
<223> OTHER INFORMATION: peptide

<400> SEQUENCE: 31

Asn Leu Pro Ala Ala Gln Arg Tyr Gly Arg Glu Leu Arg Arg Met Ser
 1               5                  10                 15
Asp Glu Phe Val Asp Ser Phe Lys Lys
            20              25

<210> SEQ ID NO 32
<211> LENGTH: 25
<212> TYPE: PRT
<213> ORGANISM: Artificial Sequence
<220> FEATURE:
<223> OTHER INFORMATION: peptide

<400> SEQUENCE: 32

Asn Leu Trp Ala Ala Gln Arg Tyr Ala Arg Glu Leu Arg Arg Met Ser
 1               5                  10                 15
Asp Glu Phe Val Ala Ala Phe Lys Lys
            20              25

<210> SEQ ID NO 33
<211> LENGTH: 25
<212> TYPE: PRT
<213> ORGANISM: Artificial Sequence
<220> FEATURE:
<223> OTHER INFORMATION: peptide

<400> SEQUENCE: 33

Asn Leu Trp Ala Ala Gln Arg Tyr Gly Arg Glu Ala Arg Arg Met Ser
 1               5                  10                 15
Asp Glu Phe Val Asp Ser Phe Lys Lys
            20              25

<210> SEQ ID NO 34
<211> LENGTH: 25
<212> TYPE: PRT
<213> ORGANISM: Artificial Sequence
<220> FEATURE:
<223> OTHER INFORMATION: peptide

<400> SEQUENCE: 34

Asn Leu Trp Ala Ala Gln Arg Tyr Gly Arg Glu Leu Arg Arg Met Ser
 1               5                  10                 15
Ala Glu Phe Val Asp Ser Phe Lys Lys
            20              25

<210> SEQ ID NO 35
<211> LENGTH: 20
<212> TYPE: PRT
<213> ORGANISM: Artificial Sequence
<220> FEATURE:
<223> OTHER INFORMATION: peptide

<400> SEQUENCE: 35
```

```
Gln Arg Tyr Gly Arg Glu Leu Arg Arg Met Ser Asp Glu Phe Val Asp
1               5                   10                  15

Ser Phe Lys Lys
            20

<210> SEQ ID NO 36
<211> LENGTH: 21
<212> TYPE: PRT
<213> ORGANISM: Artificial Sequence
<220> FEATURE:
<223> OTHER INFORMATION: peptide

<400> SEQUENCE: 36

Asn Leu Trp Ala Ala Gln Arg Tyr Gly Arg Glu Leu Arg Arg Met Ser
1               5                   10                  15

Asp Glu Phe Val Asp
            20

<210> SEQ ID NO 37
<211> LENGTH: 16
<212> TYPE: PRT
<213> ORGANISM: Artificial Sequence
<220> FEATURE:
<223> OTHER INFORMATION: peptide

<400> SEQUENCE: 37

Gly Gln Val Gly Arg Gln Leu Ala Ile Ile Gly Asp Asp Ile Asn Arg
1               5                   10                  15
```

MUTANT BCL-2 PROTEINS AND USES THEREOF

TECHNICAL FIELD OF THE INVENTION

The present invention relates to mutant Bcl-2 proteins derived from wild-type human Bcl-2. The proteins of the present invention can be used in biological assays to identify substances which block the ability of Bcl-2 to inhibit programmed cell death.

BACKGROUND OF THE INVENTION

Apoptosis or programmed cell death (hereinafter "PCD") is a highly conserved and essential feature of development and homeostasis in higher organisms. Kelekar, et al., *Molecular and Cellular Biology*, 17(12):7040–7046 (1997). Apoptosis is a mechanism by which the body replaces older cells with new healthy cells, or by which a cell destroys itself to prevent the transmission of genetic errors to its progeny. In some cancers, for example, it is generally accepted that an alteration in cell growth and/or cell death is due to the accumulation of several mutations in "key" genes which regulate these processes. The normal system is unable to eliminate cells containing these mutated genes and uncontrolled cell growth results. Thus, the aberrant nature of cell growth or apoptosis observed in cancer and other diseases is the consequence of malfunctioning of the regulatory pathways which control the equilibrium between cell growth and cell death.

One group of molecules that is involved in promoting or suppressing apoptotic responses is the Bcl-2 family of proteins. The Bcl-2 family contains proteins which either promote or inhibit cell death. Some of the inhibitors, frequently referred to as anti-apoptotic proteins, include: Bcl-2, Bcl-$x_L$, Mcl-1, adenovirus E1B 19K, Epstein-Barr virus BHRF1, and *Caenorhabditis elegans* Ced-9. Promoters of cell death, frequently referred to as pro-apoptotic proteins, include, for example: Bax, Bak, Bad, Bik, Bid and Bcl-$x_S$. An important feature of the Bcl-2 family is that its members can interact (i.e. dimerize) with themselves or other members of the family. (Kelekar, supra. Also see Ottilie, S., et al., *J of Biol. Chem.*, 272(49):30866–30872 (1997)). It is believed that these protein—protein interactions are critically important in determining a cell's response to a death signal (Kelekar, supra, also see Yang et al., *Cell*, 80:285–291 (1995)).

The three-dimensional structure of the Bcl-2 family member, Bcl-$x_L$ has been elucidated (Muchmore et al., *Nature*, 381:335–341 (1996)). The structure of Bcl-$x_L$ contains two central hydrophobic helices surrounded by amphipathic helices. A hydrophobic binding pocket, is created by the spatial proximity of three particular domains, known as BH1, BH2, and BH3, and provides a binding site for the death-promoting proteins. Sattler M., et al., *Science*, 275: 983–986 (1997). It is also known that the death-promoting proteins interact with this binding site through their BH3 domains. Id.

It is known in the art that over-expression of the anti-apoptotic proteins, such as Bcl-2 and Bcl-$x_L$ which are often present in cancerous and other diseased cells, results in the blocking of apoptotic signals and allows said cells to proliferate. For example, high levels of Bcl-2 gene expression are found in a wide variety of human cancers. Furthermore, it is believed that by blocking Bcl-2 and Bcl-$x_L$, apoptosis can be induced in diseased cells, and can provide an effective therapy for cancer and other diseases caused by the impairment of the apoptotic process. Thereupon, there is a need in the art for an assay, which can be used to identify compounds which trigger or induce apoptosis by inhibiting the interactions between the Bcl-2 family of proteins.

It is also known in the art that naturally occurring or wild-type Bcl-2 behaves poorly and aggregates when placed in solution. Such aggregation makes it difficult for researchers to use Bcl-2 in structural studies such as X-ray crystallography or NMR which can aid in the design of drugs which block the ability of Bcl-2 to inhibit programmed cell death. Additionally, the aggregation of Bcl-2 in solution also makes it difficult to use naturally occurring or wild-type Bcl-2 protein in assays to identify substances which block the ability of Bcl-2 to inhibit programmed cell death. Therefore, there is a need in the art to develop an altered or mutated form of Bcl-2 that does not aggregate in solution and which can be used in structural studies. However, thus far, efforts to develop such an altered or mutated protein have been unsuccessful. For example, Anderson et al. in *Protein Expression and Purification*, 15:162–170 (1999), describe the cloning and expression of a recombinant human Bcl-2 referred to as "rhBcl-2". In this mutant form of Bcl-2, the putative flexible loop of Bcl-2 is truncated and replaced with a flexible linker which consists of four (4) alanine residues. In addition, the hydrophobic carboxy terminus of Bcl-2 is replaced with six (6) histidine residues. Specifically, the Anderson et al. Bcl-2 deletion mutant can be summarized as follows: Bcl-$2_{(6-32)}$-AAAA-Bcl-$2_{(56-206)}$-HHHHHH. While Anderson et al. were able to successfully express their mutant in *E. Coli* and purify it, they noted that the solubility limit for their expressed protein was lower than ideal for X-ray or NMR-based structural studies under the examined conditions. Thereupon, a need currently exists in the art for an altered or mutant form of Bcl-2 which can be used in X-ray or NMR-based structural studies. There is also a need for screening assays to identify compounds that are capable of binding to Bcl-2. Such screening assays can be achieved with a water soluble Bcl-2 mutant.

SUMMARY OF THE INVENTION

The present invention relates to a mutant protein derived from a wild-type human Bcl-2 protein. More specifically, in the mutant proteins of the present invention, a sequence of amino acid residues comprising a flexible loop from the wild-type human Bcl-2 protein is replaced with a different sequence (i.e. a replacement amino acid sequence) comprising at least two acidic amino acids. The acidic amino acids may be glutamic acid or aspartic acid or a combination of both. Preferably, the replacement amino acid sequence comprises a sequence of at least a portion of a flexible loop from human Bcl-$x_L$ protein. More preferably, the replacement amino acid sequence comprises the sequence of SEQ ID NO: 1. A particularly preferred mutant protein has the amino acid sequence of SEQ ID NO:2.

In one embodiment of the invention, the replacement amino acid sequence of the mutant protein comprises a sequence of at least 4 to about 50 amino acid residues. More preferably, the replacement amino acid sequence comprises a sequence of at least 16 to about 25 amino acid residues.

The mutant proteins of the invention have an isoelectric point lower than that of wild-type Bcl-2. Preferably, the isoelectric point is from 4.5 to about 6.0 and more preferably, from 5.0 to about 5.5. A particularly preferred isoelectric point is 5.0.

The present invention also relates to an assay for identifying substances which bind to a Bcl-2 protein, the assay comprising the steps of (a) providing a candidate substance to be tested; (b) providing a labeled peptide which is capable of binding tightly to a mutant protein of the invention; (c) forming a complex of the labeled peptide with the mutant protein; (d) forming a reaction mixture by contacting the candidate substance with the labeled peptide/mutant protein complex; (e) incubating the reaction mixture under conditions sufficient to allow the candidate substance to react and displace the labeled peptide; and (f) determining the amount of labeled peptide that has been displaced from binding to said mutant protein. Preferably, the peptide is labeled with a radioisotope, fluorescent moiety, enzyme, specific binding molecule or particle. More preferably, the peptide is labeled with a fluorescein compound. Most preferably, the peptide is labeled with fluorescein isothiocyanate or 5-carboxy-fluorescein.

BRIEF DESCRIPTION OF THE FIGURES

FIG. 3 shows a Ribbons representation of the NMR-derived structure of (A) Bcl-2/iso1 and (B) Bcl-2/iso2.

DETAILED DESCRIPTION OF THE INVENTION

1. The Present Invention

The present invention relates to mutant Bcl-2 proteins which do not aggregate in solution and can be used in assays to identify substances which bind to a Bcl-2 protein.

II. Sequence Listing

The present application also contains a sequence listing. For the nucleotide sequences, the base pairs are represented by the following base codes:

| Symbol | Meaning |
|--------|---------|
| A | A; adenine |
| C | C; cytosine |
| G | G; guanine |
| T | T; thymine |
| U | U; uracil |
| M | A or C |
| R | A or G |
| W | A or T/U |
| S | C or G |
| Y | C or T/U |
| K | G or T/U |
| V | A or C or G; not T/U |
| H | A or C or T/U; not G |
| D | A or G or T/U; not C |
| B | C or G or T/U; not A |
| N | (A or C or G or T/U) |

The amino acids shown in the application are in the L-form and are represented by the following amino acid-three letter abbreviations:

| Abbreviation | Amino acid name |
|--------------|-----------------|
| Ala | L-Alanine |
| Arg | L-Arginine |
| Asn | L-Asparagine |
| Asp | L-Aspartic Acid |
| Asx | L-Aspartic Acid or Asparagine |
| Cys | L-Cysteine |
| Glu | L-Glutamic Acid |
| Gln | L-Glutamine |
| Glx | L-Glutamine or Glutamic Acid |
| Gly | L-Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Xaa | L-Unknown or other |

III. Proteins of the Present Invention

The present invention relates to mutant Bcl-2 proteins derived from the naturally occurring or wild-type human Bcl-2 protein. More specifically, the mutant proteins of the present invention are chimeric proteins that contain amino acid residues derived from wild-type human Bcl-2 protein but which exhibit a lower isoelectric point than the wild-type protein. Accordingly, unlike naturally occurring or wild-type human Bcl-2 protein, the mutant Bcl-2 proteins of the present invention do not aggregate in solution. In a preferred embodiment, the mutant proteins of the present invention comprise amino acid residues derived from wild-type human Bcl-$x_L$ protein as well as from the naturally occurring or wild-type human Bcl-2 protein. Because the mutant Bcl-2 proteins of the present invention do not aggregate when placed in solution, these proteins can be used in X-ray crystallography and NMR structural studies as well as in assays to identify candidate compounds which block the ability of Bcl-2 to inhibit programmed cell death.

As used herein, the term "isoelectric point" (or pI) refers to the pH at which the protein carries no net charge. The isoelectric points of Bcl-2/iso1, Bcl-2/iso2, and Bcl-2/iso3 are about 7.0, 7.2 and 7.2, respectively. The mutant proteins of the present invention have an isoelectric point lower than that of wild-type Bcl-2 and preferably, in the range of 4.5 to about 6.0. More preferably, the isoelectric point of a mutant protein of the invention is from 4.5 to about 5.5. A more preferred isoelectric point is from about 5.0 to about 5.5. A most preferred isoelectric point is 5.0. Means for determining the isoelectric point of a protein are well known to those of ordinary skill in the art.

Figure 1:
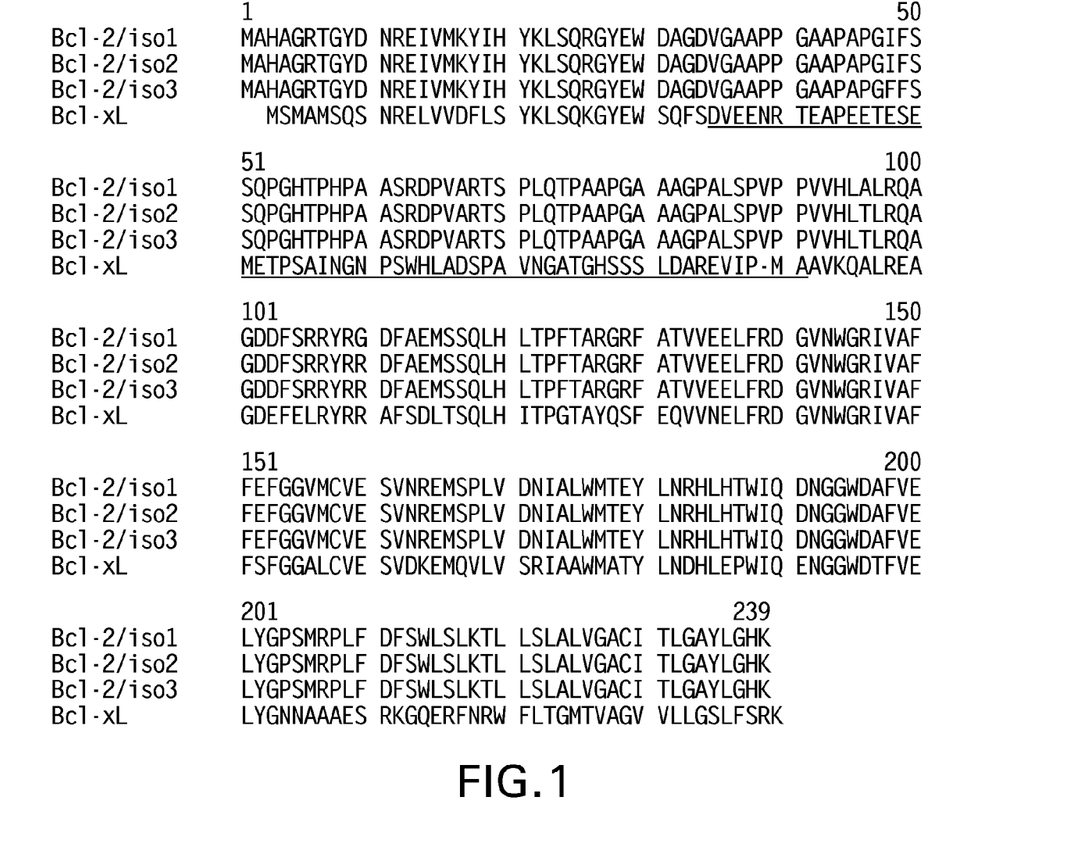
FIG. 1 shows the wild-type amino acid sequences for the Bcl-2 isoforms 1, 2, and 3 (hereinafter Bcl-2/iso1 (SEQ ID NO:3), Bcl-2/iso2 (SEQ ID NO:4), and Bcl-2/iso3 (SEQ ID NO:5, respectively) and the wild-type sequence of human Bcl-$x_L$ protein. The differences between Bcl-2/iso1, Bcl-2/iso2, and Bcl-2/iso3 are highlighted in bold. The putative unstructured loop (amino acid residues 35–91) is underlined.
Figure 2:
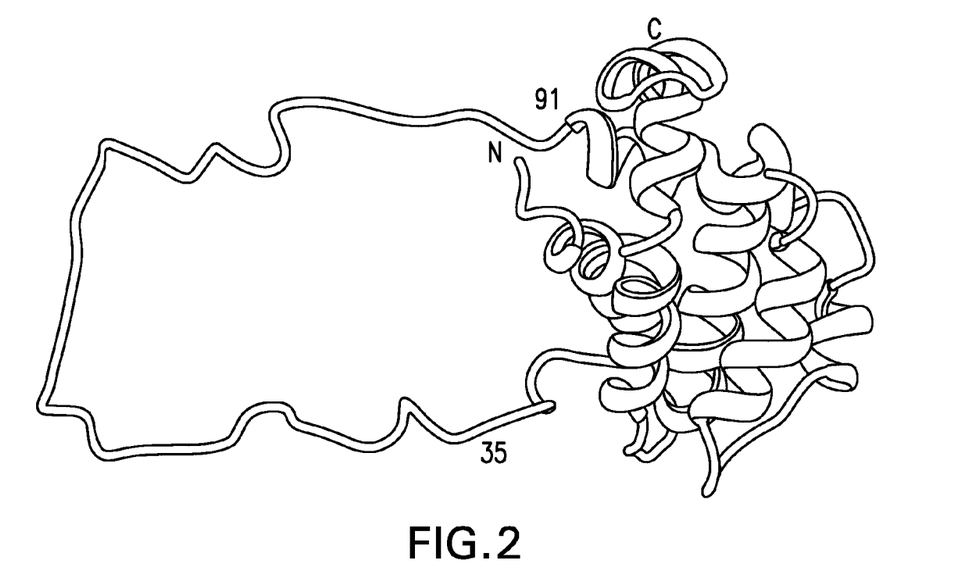
FIG. 2 shows a Ribbons representation of wild-type human Bcl-$x_L$. The unstructured loop is shown as the uncoiled ribbon projecting to the left in the Figure.

As used herein, the term "naturally occurring" or "wild-type" human Bcl-2 protein refers to any of three proteins which are isoforms of human Bcl-2. These isoforms are shown as SEQ ID NOS:3, 4, and 5. The protein shown in SEQ ID NO:3 is referred to as "isoform 1" (Bcl-2/iso1) and is described in Tsujimoto, Y. et al., *Science*, 226:1097–1099 (1984) and Tsujimoto, Y. et al., *PNAS*, 83:5214–5218 (1986). The protein shown in SEQ ID NO:4 is referred to as "isoform 2" (Bcl-2/iso2) and is described in Cleary, M. and Sklar. K., *PNAS,* 82:7439–7443 (1985) and Cleary, M. et al., *Cell,* 47:19–28 (1986). The protein shown in SEQ ID NO:5 is referred to as "isoform 3" (Bcl-2/iso3) and is described in Bakshi, A. et al., *Cell,* 41:899–906 (1985) and Seto, M. et al, *EMBO J.* 7:123–131(1988). As can be seen in FIG. 1, Bcl-2/iso3 differs from Bcl-2/iso1 and Bcl-2/iso2 at residue position 48 (F in place of I) Bcl-2/iso 1 differs from the other two isoforms at residue positions 96 and 110 (A and G in place of T and R, respectively).

As used herein, the term "naturally occurring" or "wild-type" human Bcl-$x_L$ protein refers to the protein shown in SEQ ID NO:6 and described in *Cell,* 74:597–608 (1993).

As used herein, the term "about", when used to modify an isoelectric point, means ±5%. When used to modify a length of amino acid sequence, "about" means ±2 amino acids.

Naturally occurring or wild-type human Bcl-$x_L$ protein contains an unstructured flexible loop (meaning, that it shows no regular secondary structure such as an α-helix or β-sheet) that is not required for maintaining the integrity of the protein in solution (Muchmore et al., *Nature,* 381: 335–341 (1996)). This loop is found at amino acid residues 35–91 (see FIG. 1 and SEQ ID NOS:6). It is known in the art that the Bcl-$x_L$ protein retains it function as an anti-apoptotic protein even when this loop is removed from the protein. Based on the sequence homology between Bcl-$x_L$ and Bcl-2, residues 35–91 of Bcl-2 also are presumed to be unstructured and unnecessary for maintaining the integrity of the protein. These unstructured loops are points of post-translational modification such as phosphorylation.

The mutant proteins of the present invention are derived from human Bcl-2 protein. Specifically, the mutant human Bcl-2 proteins of the present invention have the amino acid residues which form its unstructured, flexible loop replaced with at least 4 to about 50 amino acid residues of which at least two are acidic amino acids, i.e. glutamic acid (Glu) or aspartic acid (Asp). The acidic amino acids may be located at any position within the replacement sequence. Furthermore, the replacement sequence may comprise only one type of acidic amino acid (i.e. either two or more Glus or two or more Asps) or a combination of both. As intended by this description, there is no limit on the type or total number of acidic amino acids comprising the replacement sequence (as long as it comprises at least two acidic amino acids).

In a preferred embodiment, the unstructured, flexible loop of the human Bcl-2 protein is replaced with a sequence of at least 4 to about 50 amino acid residues corresponding to a contiguous sequence of amino acid residues from the unstructured loop of Bcl-$x_L$ wherein at least two of the residues are acidic amino acids. More preferably, the amino acid residues of the unstructured, flexible loop of Bcl-2 are replaced with at least 16 to about 25 amino acid residues (of which at least two are acidic amino acids) from the corresponding, unstructured, flexible loop from human Bcl-$x_L$ protein. Even more preferably, the entire sequence of the unstructured, flexible loop of Bcl-2, from amino acid residues 35–91, is replaced with the sequence DVEENRTEAPEGTESE (SEQ ID NO:1) which encode a portion of the flexible loop of the naturally occurring or wild-type human Bcl-$x_L$ protein.

The mutant Bcl-2 proteins of the present invention can contain from about 150 to about 180 amino acid residues.

An example of a preferred mutant Bcl-2 protein of the present invention includes, but is not limited to:

MAHAGRTGYDNREIVMKYIHYKLSQRGYEWDAGD-DVEENRTEAPEGTESEVVHLALRQAGDDFSRRYRG-DFAEMSSQLHLTPFTARGRFATVVEELFRDGVNWGR-IVAFFEFGGVMCVESVNREMSPLVDNIALWMTEYLN-RHLHTWIQDNGGWDAFVELYGPSMR (SEQ ID NO:2).

As discussed previously, the mutant Bcl-2 proteins of the present invention do not aggregate in solution unlike the naturally occurring or wild-type Bcl-2 protein. While not wishing to be bound by any theory, the inventors of the present invention believe that that the substitution of a portion of the unstructured, flexible loop from the human Bcl-$x_L$ protein for the entire unstructured, flexible loop from Bcl-2, makes the mutant Bcl-2 proteins of the present invention more acidic and thus reduces the isoelectric point of the mutant Bcl-2proteins compared to the naturally occurring or wild-type Bcl-2-protein. More specifically, the inventors found that when amino acid residues 49–91 were removed from the unstructured flexible loop of Bcl-$x_L$, this shortened protein behaved well in solution and did not aggregate. The isoelectric point of this shortened Bcl-$x_L$ protein was determined to be about 4.9. The inventors then removed the same amino acid residues (49–91) from the unstructured, flexible loop of Bcl-2. Surprisingly, this shortened protein did not behave well in solution and exhibited aggregation. The isoelectric point of this shortened Bcl-2 protein was determined to be about 6.4. The inventors compared the shortened loops of the Bcl-$x_L$ and Bcl-2 proteins and realized that the shortened loop from Bcl-$x_L$ contained more acidic amino acid residues than the shortened loop from Bcl-2, thus giving the shortened Bcl-$x_L$ protein a lower isoelectric point than the shortened Bcl-2 protein. The inventors believe that the difference in the isoelectric points explains the difference in the behavior of the two proteins.

The mutant proteins of the present invention have an isoelectric point below about 6.0, preferably below about 5.5. More specifically, the inventors found that when the entire sequence of the unstructured, flexible loop of Bcl-2, from amino acid residues 35–91 is replaced with the amino acid residues DVEENRTEAPEGTESE (SEQ ID NO:1) (which represent a portion of the flexible loop of the naturally occurring or wild-type human Bcl-$x_L$ protein), the isoelectric point of this mutant Bcl-2 protein is about 5.0. The inventors believe that this reduction in the isoelectric point in the mutant Bcl-2 protein of the present invention when compared to the wild-type Bcl-2 protein accounts for why the mutant Bcl-2 proteins do not aggregate in solution.

The mutant proteins of the present invention can be prepared using techniques known in the art, such as by recombinant DNA techniques. For example, a nucleotide sequence encoding a Bcl-2 mutant protein as described above, can be inserted into a suitable DNA vector, such as a plasmid. More specifically, the nucleotide sequence can be inserted into a suitable DNA vector using techniques known in the art, including, but not limited to, blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are described in Sambrook, J., et al., *Molecular Cloning. A Laboratory Manual,* 2d Ed., Cold Spring Harbor Laboratory Press, Plainview, N.Y., (1989). Once prepared the nucleotide sequence is inserted into the DNA vector, the vector is used to transform a suitable host. The recombinant mutant protein is produced in the host by expression. The transformed host can be either a prokaryotic or eukaryotic cell.

Once the proteins of the present invention have been prepared, they may be substantially purified by a number of chromatographic procedures, including ion exchange, affinity, size exclusion or hydrophobic interaction (see Crighton, T., *Proteins, Structures and Molecular Principles*, WH Freeman and Co., New York, N.Y. (1983)). The composition of any synthetic proteins of the present invention can be confirmed by amino acid analysis or sequencing (using the Edman degradation procedure). The mutant proteins of the present invention can be used in screening assays. More specifically, the mutant proteins of the present invention can be used to identify small molecules that block the ability of Bcl-2 to inhibit programmed cell death.

IV. Screening Assays Using the Proteins of the Present Invention

The present invention also relates to a variety of screening assays to identify candidate compounds that are capable of binding to the mutant Bcl-2 proteins of the present invention and thus inhibit programmed cell death. The assay of present invention focuses on the ability or inability of candidate compounds to bind to the mutant Bcl-2 proteins of the present invention and displace a labeled probe molecule such as a peptide.

The screening assays of the present invention can be used to screen large numbers of compounds to identify those compounds which are capable of binding to Bcl-2. Compounds which are identified as binding to Bcl-2 can be used clinically as anti-cancer agents. Specifically, these compounds can be used to promote apoptosis in cancer cells that over express Bcl-2 the treatment of certain cancers. Compounds which do not have activity in the screening assays can be eliminated from further consideration as candidate compounds.

The candidate compounds to be screened can encompass numerous chemical classes. However, the candidate compounds are typically organic molecules, preferably small organic compounds having a molecular weight of from about 150 to about 800 daltons. Such candidate compounds shall contain functional groups necessary for structural interaction with proteins, particularly hydrogen bonding, and typically include at least an amine, carbonyl, hydroxyl or carboxyl group, preferably at least two of the functional chemical groups. The candidate compounds often contain cyclical carbon or heterocyclic structures and/or aromatic or polyaromatic structures substituted with one or more of the above functional groups. Candidate compounds can also be found among biomolecules including peptides, saccharides, fatty acids, steroids, purines, pyrimidines, derivatives, structural analogs or combinations thereof.

Candidate compounds can be obtained from a wide variety of sources such as libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

In competitive binding assays, the candidate compound can compete with a labeled analyte for specific binding to sites on a binding agent bound to a solid surface. In such an assay, the labeled analyte can be a labeled peptide and the binding agent can be the mutant Bcl-2 protein of the present invention bound to the solid phase. The concentration of labeled analyte bound to the binding agent is inversely proportional to the ability of the candidate compound to compete in the binding assay. The amount of inhibition of labeled analyte by the candidate compound depends on the binding assay conditions and on the concentrations of binding agent, labeled analyte, and candidate compound that are used. Under specified assay conditions, a candidate compound is said to be capable of binding to the mutant Bcl-2 protein of the present invention in a competitive binding assay, if the amount of binding of the labeled analyte to the binding agent is decreased by ten percent (10%) or more. In a direct binding assay, a candidate compound binds to the mutant Bcl-2 protein of the present invention when the signal measured is twice the background level or higher.

In a competitive binding assay, the candidate compound competes with the labeled analytes for binding to the mutant Bcl-2 protein of the present invention. As described herein, the binding agent can be bound to a solid surface to effect separation of bound labeled analyte from the unbound labeled analyte. Alternatively, the competitive binding may be conducted in a liquid phase, and any of a variety of techniques known in the art may be used to detect the release of the bound labeled analyte or to separate the bound labeled analyte from the unbound labeled analayte. Following separation, the amount of bound labeled analyte is determined. The amount of protein present in the sample is inversely proportional to the amount of bound labeled analyte.

Alternatively, a homogenous binding assay can be performed in which a separation step is not needed. In these types of assays, binding of the candidate compound to the mutant Bcl-2 protein results in displacement of a labeled analyte, and subsequent change in signal emitted by the analyte.

An example of a competitive binding assay for detecting candidate compounds capable of binding of the mutant Bcl-2 proteins of the present invention is described in Example 2 herein.

As discussed hereinbefore, the screening assays described herein employ one or more labeled molecules. The label used in the assay of the present invention can directly or indirectly provide a detectable signal. Various labels that can be used include radioisotopes, fluorescent compounds, chemiluminescent compounds, bioluminescent compounds, enzymes, specific binding molecules, particles, e.g., magnetic particles, and the like. Specific binding molecules include pairs, such as biotin and streptavidin, digoxin and antidigoxin, etc. For the specific binding members, the complementary member is normally labeled with a molecule that provides for detection, in accordance with known procedures. Furthermore, the binding of these labels to the mutant proteins of the present invention is accomplished using standard techniques known in the art.

A variety of other reagents may also be included in the screening assay. These include reagents like salts, neutral proteins, e.g., albumin, detergents, etc. that are used to facilitate optimal protein—protein binding and/or reduce non-specific or background interactions. Reagents that improve the efficiency of the assay, such as protease inhibitors, nuclease inhibitors, anti-microbial agents, etc., may be used. The mixture of components are added in any order that provides for the requisite binding. Incubations are performed at any suitable temperature, typically between about 0 and about 40° C. Incubation periods are selected for optimum activity. Typically, incubations from about 0.05 and 10 hours will be sufficient.

By way of example, and not of limitation, examples of the present invention shall now be given.

EXAMPLE 1

Preparation of Mutant Bcl-2 Proteins

Construction of plasmids. Nucleic acid constructs were prepared for producing mutant Bcl-2 proteins which were subsequently evaluated for their suitability for NMR structural studies. All reagents used in the generation of these constructs were obtained from commercially available sources. Generally, nucleic acid fragments were prepared by standard PCR techniques and cloned into commercial vectors by means well known in the art. All sequences were confirmed by analysis on an ABI Prism 377 DNA sequencer (PE Applied Biosystems, Foster City, Calif.). The forward and reverse primers used to amplify the PCR fragments are shown in Table I below.

TABLE 1

| Fragment Sequence | SEQ ID NO: |
|---|---|
| 5'-CACTCACCATATGGCTCACGCTGGGAGAACGGGGTACGACAAC-3' | 7 |
| 5'-GCGAGCTCTCGAGCTTCAGAGACAGCCAGGAGAAATCAAACAG-3' | 8 |
| 5'-GCCCCAGAAGGGACTGAATCGGAGGTGGTCCACCTGGCCCTCCGCCAA-3' | 9 |
| 5'-CTCAGTACGGTTCTCTTCCACATCATCTCCCGCATCCCACTCGTAGCC-3' | 10 |
| 5'-CACTCACCATATGGCTCACGCTGGGAGAACGGGGTACGACAAC-3' | 11 |
| 5'-GCGAAGCTCTCGAGCTATCAATCAAACAGAGGCCGCATGCTGGGGCCGTA-3' | 12 |
| 5'-GAGGTGGTCCACCTGACCCTCCGCCAAGCCG-3' | 13 |
| 5'-CGGCTTGGCGGAGGGTCAGGTGGACCACCTC-3' | 14 |
| 5'-GCCGCTACCGCCGCGACTTCGCCGAG-3' | 15 |
| 5'-CTCGGCGAAGTCGCGGCGGTAGCGGC-3' | 16 |

A fragment encoding amino acids 1–218 of Bcl-2 first was prepared by reverse transcriptase polymerase chain reaction (RT-PCR), using an RT-PCR kit from BOEHRINGER-MANNHEIM Corp. (Indianapolis, Ind.). The fragment was generated using primer sequences SEQ ID NO:7 and SEQ ID NO:8 and Daudi mRNA (CLONTECH, Palo Alto, Calif.) as a template, under conditions suggested by the manufacturer. The fragment initially was cloned into NdeI and XhoI sites of the plasmid pET30b (Novagen, Madison, Wis.) for expression. The resulting plasmid was termed plasmid A.

A second plasmid (plasmid B) then was generated which contained fragments encoding amino acids 1–34 of SEQ ID NO:3 (Bcl-2/iso1), amino acids 29–44 of SEQ ID NO:6 (Bcl-$x_L$ loop) and 92–218 of SEQ ID NO:3 (Bcl-2/iso1). The fragments were generated with an ExpandLong PCR kit (BOEHRINGER-MANNHEIM Corp., Indianapolis, Ind.) using SEQ ID NOS:9 and 10 as primers, plasmid A as template and the following cycle conditions: One cycle at 94° C., 4 min., one cycle at 94° C., 40 sec., 15 cycles at 55° C., 45 sec; 68° C., 6 min and 1 cycle at 72° C., 10 min. The primer sequences were designed in such a manner so as to (1) amplify in a "backward" direction in order to omit the intervening sequence of plasmid A (containing the nucleotides which encode for amino acids 35–91 of SEQ ID NO: 3) and (2) contain nucleotides which encode for the Bcl-$x_L$ loop (amino acids 29–44 of SEQ ID NO: 6). Subsequent ligation of the amplified fragment resulted in plasmid B.

A third plasmid (plasmid C) was constructed which contained a fragment encoding amino acids 1–34 of SEQ ID NO:3 (Bcl-2/iso1), amino acids 29–44 of SEQ ID NO:6 (Bcl-$x_L$ loop) and 92–207 of SEQ ID NO: 3 (Bcl-2/iso1). A fragment was generated from plasmid B (as template), using standard PCR reagents, Pfu DNA polymerase, and SEQ ID NOS:11 and 12 as primers with the following cycle conditions: One cycle at 94° C., 4 mins., thirty cycles at 94° C., 30 sec.; 55° C., 45 sec; 72° C., 2 min., one cycle at 72° C., 10 min. The resulting fragment was cloned into the NdeI and XhoI sites of pET28b (Novagen, Madison, Wis.), forming plasmid C.

For constructing the plasmid for Bcl-2/iso2 (plasmid D), plasmid C was used as a DNA template. Alanine 96 and glycine 110 were changed to threonine 96 and arginine 110 respectively, using two sets of primers: SEQ ID NOS:13 and 14 (for the Ala96 to Thr96 mutation) and SEQ ID NOS:15 and 16 (for the Gly110 to Arg 110 mutation). The mutated sequences were obtained using a Stratagene® Quick Change kit (Stratagene®, La Jolla, Calif.) in accordance with the manufacturer's directions.

Expression and purification of Bcl-2 mutein: The Bcl-2 muteins were expressed in *E. coli* BL21(DE3) cells grown in M9 medium containing $^{15}NH_4Cl$, $^{15}NH_4Cl$ plus [U-$^{13}$C] glucose, or $^{15}NH_4Cl$, [U-$^{13}$C]glucose, and 75% $^2H_2O$. Cells were induced with 1 mM isopropyl-D-thioglactopyranoside for 3 hours at 30° C. during mid-log phase. Cells were resuspended in 20 mM Tris-Cl, pH 7.8, 1.5 M NaCl, 5 mM 2-mercaptoethanol, and then lysed by French Press. The soluble fraction was loaded over $Ni^{2+}$-agarose column, washed with the same column buffer, then washed with 20 mM imidazole, 20 mM Tris-Cl, pH 7.8, 1.5 M NaCl, 5 mM 2-mercaptoethanol, and finally eluted with 500 mM imidazole, 20 mM Tris-Cl pH 7.8, 5 mM 2-mercaptoethanol. The eluted Bcl-2 fraction was treated with biotinylated thrombin according to the suggested protocol of the manufacturer (Novagen, Madison, Wis.). Biotinylated thrombin (0.5 units) was used to cleave 1 mg of protein for 16 hours at room temperature. The cleavage reaction was stopped by adding Streptavidin Agarose (Novagen, Madison, Wis.), diluted three fold with 20 mM Tris-Cl, pH 7.5, and passed over another pre-equilibrated $Ni^{2+}$ column. The non-his tagged flow through Bcl-2 fraction was collected. The purified Bcl-2 mutein was concentrated and stored at 4° C. N-terminal protein sequencing for the purified Bcl-2 mutein was carried out on 477A Protein Sequencer (PE Applied Biosystem, Forster City, Calif.). The protein concentration was determined using a Coomassie protein assay kit from Pierce (Rockford, Ill.) and UV.

EXAMPLE 2

Competitive Binding Assays to Measure Peptide Affinities for Bcl-2/iso1

A competitive fluorescence polarization assay was used to measure the affinity of various peptides for Bcl-2/iso1 (see Table 2) or Bcl-2/iso2 (see Table 3). Competitive assays were performed using one of the following three fluorescein-labeled peptides as a probe:

(1) (5-FAM)-AAAAAQRYGRELRRMSDEFVDSFKK (SEQ ID NO:17), obtained from Synpep Corporation, Dublin, Calif., (2) (5-FAM)-AAAAAQRYGRELRRMSDEFVDSKK (SEQ ID NO:18), or (3) (FITC)-AAQRYGRELRRMSDEFVR(SEQ ID NO:19). The dissociation constants of these fluoresceinated peptides from Bcl-2/iso1 are ~20 nM, ~50 nM, and ~100 nM, respectively.

All titrations were automated by means of an Abbott clinical diagnostics instrument (IMx, FPIA mode) modified with a special protocol for performing titrations. A complete two-fold dilution series, comprised of twenty separate 2 mL samples, was obtained by delivering appropriate individual aliquots to the first seven tubes, aliquots from an intermediate diluted stock for the next seven, and one more intermediate dilution for the final six. Dilution buffer for all stocks and samples was 120 mM sodium phosphate at pH 7.55 with 0.01% bovine gamma globulin and 0.1% sodium azide. The concentrations of the DMSO stock solutions of the peptide were 1–4 mM as determined by Trp absorbance (O.D. 280 nm), Tyr absorbance (O.D. 293), or amino acid analysis. The final DMSO concentration for all samples never exceeded 1%. Twenty 1.8 uL samples were prepared without fluoresceinatedpeptide and read as blanks. To each tube, 0.2 uL of a Bcl-2, fluoresceinatedpeptide mixture was added; the tubes were incubated for 5 min at 35° C., and then read for total intensity and polarization. Free and bound values for the fluoresceinatedpeptide were constant within a range ±5 mP. Final Bcl-2 concentration was 340 nM. Comparisons with other, lower Bcl-2 concentrations, were made for the wild type Bcl-2 peptide. Additional controls using buffer lacking BGG showed that non-specific binding to BGG was negligible.

Steady state polarization data can be analyzed to extract the fractions of bound and free fluorescent ligand owing to the linear additivity of their anisotropy values, weighted by their respective fractional intensities (Lakowicz, JR. *Principles of Fluorescence Spectroscopy*. New York, N.Y.: Plenum Press (1983)). Nonlinear least squares curve fitting of titration data to a model for simple equilibrium binding of the fluoresceinated peptide to Bcl-2 was accomplished by programming standard binding equations, solved in terms of bound, free, and observed anisotropy values, into the model development program MINSQ (V. 4.03, Micromath Scientific Software). To determine affinities of nonfluorescent peptides, the analytical approach for equilibrium competition binding taken by Dandliker and coworkers was used, again employing MINSQ for fitting of titration curves (Dandliker, et al., *Methods in Enzymology* 74: 3–28 (1981)). Confirmation of the validity of these experimental and fitting procedures was obtained by comparing results after performing fluorescenated peptide binding, and competition binding titrations at different fixed Bcl-2 or fluoresceinated peptide concentrations.

TABLE 2

Peptide Binding to Bcl-2/iso1

| Sequence | SEQ. ID NO: | $K_d$ (nM) |
|---|---|---|
| NLWAAQRYGRELRRMSDEFVDSFKK | 20 | 14 |
| ALWAAQRYGRELRRMSDEFVDSFKK | 21 | 211 |
| NAWAAQRYGRELRRMSDEFVDSFKK | 22 | 75 |
| NLAAAQRYGRELRRMSDEFVDSFKK | 23 | 39 |
| AAAAAQRYGRELRRMSDEFVDSFKK | 17 | 74 |
| NLWGAQRYGRELRRMSDEFVDSFKK | 24 | 159 |
| NLWAGQRYGRELRRMSDEFVDSFKK | 25 | 105 |
| NLWAAQRYGRELRRMSDEFVDAFKK | 26 | 26 |
| NLWAAQRYGRELRRMSDEFVDSAKK | 27 | 397 |
| NLWAAQRYGRELRRMSDEFVDSFAK | 28 | 123 |
| NLWAAQRYGRELRRMSDEFVDSFKA | 29 | 22 |
| GGGAAQRYGRELRRMSDEFVDSFKK | 30 | 63 |
| NLPAAQRYGRELRRMSDEFVDSFKK | 31 | 54 |
| NLWAAQRYARELRRMSDEFVAAFKK | 32 | 186 |
| NLWAAQRYGREARRMSDEFVDSFKK | 33 | 7483 |
| NLWAAQRYGRELRRMSAEFVDSFKK | 34 | 762 |
| QRYGRELRRMSDEFVDSFKK | 35 | 711 |
| NLWAAQRYGRELRRMSDEFVD | 36 | 2326 |

TABLE 3

Peptide Binding to Bcl-2/iso2

| Sequence | SEQ. ID NO: | $K_d$ (nM) |
|---|---|---|
| NLWAAQRYGRELRRMSDEFVDSFKK | 20 | 8 |
| GQVGRQLAIIGDDINR | 37 | 1600 |

As Tables 2 and 3 show, the mutant proteins of the invention can be used for identifying compounds which bind tightly to a Bcl-2 family member.

EXAMPLE 3

Structure Determination of Bcl-2/iso 1 and Bcl-2/iso2 by NMR

Figure 3A:
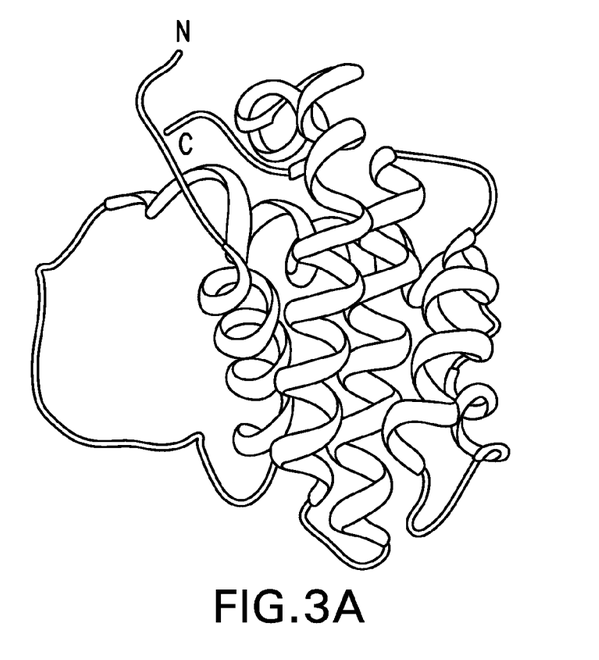
Figure 3B:
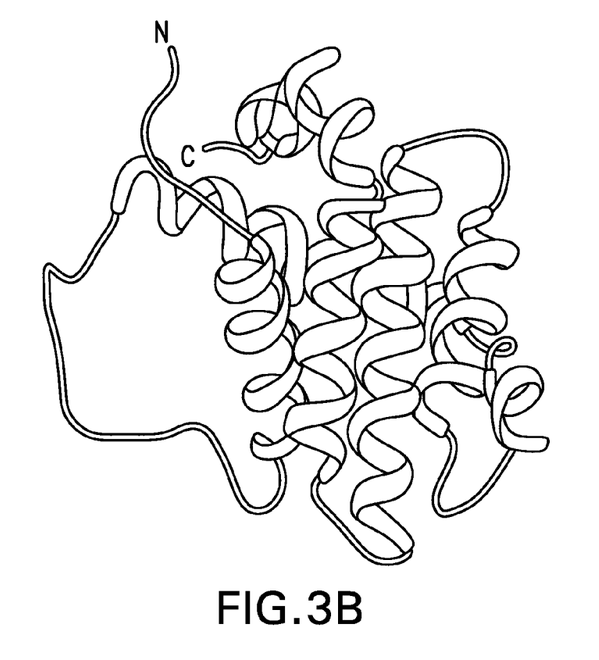

NMR Spectroscopy: The structures of soluble Bcl-2/iso1 and Bcl-2/iso2 were determined by NMR spectroscopy (see FIG. 3). All NMR experiments were acquired at 298 K on a Bruker DRX500, DRX600 or DRX800 NMR spectrometer. Backbone $^1H$, $^{13}C$, and $^{15}N$ resonance assignments were achieved with [$^{15}N$,$^{13}C$,(75%)$^2H$] Bcl-2 using a suite of deuterium-decoupled, triple-resonance experiments (HNCA, HN(CO)CA, HN(CA)CB, HN(COCA)CB, HNCO and HN(CA)CO) (Yamazaki, T., Lee, W., Arrowsmith, C. H., Muhandiram, D. R. & Kay, L. E. (1994) *J. Am. Chem. Soc.* 116, 11655–11666). The side-chain $^1H$ and $^{13}C$ NMR signals were assigned from HCCH-TOCSY experiments (Clore, G. M. & Gronenborn, A. M. (1994) *Methods Enzymol* 239, 349–63), and stereospecific assignments of the valine and leucine methyl groups were obtained from an analysis of the $^{13}C$—$^{13}C$ coupling patterns observed for biosynthetically directed, fractionally $^{13}C$-labeled Bcl-2 (Neri, D., Szyperski, T., Otting, G., Senn, H. & Wüthrich, K. (1989) *Biochemistry* 28, 7510–7516). NOE distance restraints were obtained from three-dimensional $^{15}N$— and $^{13}C$-edited NOESY spectra (Fesik, S. W. & Zuiderweg, E. R. P. (1988) *J. Magn. Reson.* 78, 588–593, Marion, D., Driscoll, P. C., Kay, L. E., Wingfield, P. T., Bax, A., Gronenborn, A. M. & Clore, G. M. (1989) *Biochemistry* 29, 6150–6156) acquired with a mixing time of 80 ms. Slowly exchanging amide protons were identified in an $^{15}N$-HSQC spectrum recorded immediately after exchanging the protein into a buffer prepared with D$_2$O. Residual dipolar couplings (HN—N and C'–C$^\alpha$) were measured using undecoupled versions of the HNCO experiment on [$^{15}$N,$^{13}$C,(75%)$^2$H] Bcl-2 in the presence of 17 mg mL$^{-1}$ Pf1 phage (Tjandra, N. (1999) *Structure* 7, R205–R211, Hansen, M. R., Mueller, L. & Pardi, A. (1998) *Nature Struc. Biol.* 5, 1065–1074, Clore, G. M., Starich, M. R. & Gronenborn, A. M. (1998) *J. Am. Chem. Soc.* 120, 1–571-10572).

Structure Calculations: Bcl-2 structures were calculated using a simulated annealing protocol (Brunger, A. T. (1992) X-PLOR Version 3.1. (Yale University Press, New Haven and London) with the program CNX (MSI, San Diego). A square-well potential (F$_{NOE}$=50 kcal mol$^{-1}$) was employed to constrain NOE-derived distances. Based on the cross peak intensities, NOE-derived distance restraints were given upper bounds of 3.0, 4.0, 5.0, or 6.0 Å. Torsion angle restraints ϕ, ψ were generated from analysis of N, C', C$^\alpha$, and H$^\alpha$ chemical shifts using the TALOS program (Cornilescu, G., Delaglio, F. & Bax, A. (1999) *J. Biomol. NMR* 13, 289–302). A force constant of 200 kcal mol$^{-1}$ rad$^{-2}$ was applied to all torsional restraints. Explicit hydrogen bonds were included in α-helices only for residues observed to have slowly exchanging amide protons. The program PROCHECK was employed to analyze the geometric quality of the calculated structures in the ensemble (Laskowski, R. A., MacArthur, M. W., Moss, D. S. & Thornton, J. M. (1993) *J. Appl. Cryst.* 26, 283–291).

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

Any references referred to herein are incorporated by reference.

What is claimed is:

1. A mutant protein having an amino acid sequence comprising:
MAHAGRTGYDNREIVMKYIHYKLSQRGYEWDAGDDVEENRTEAPEGTESEVVHLALRQAGDDFSRRYRGDFAEMSSQLHLTPFTARGRAFTVVEELFRDGVNWG RIVAFFEFGGVMCVESVNREMSPLVDNIALWMTEYLRHLHTWIQDNGGWDAFVELYGPSMR (SEQ ID NO: 2).

* * * * *